United States Patent [19]
Vickers

[11] Patent Number: 5,677,536
[45] Date of Patent: Oct. 14, 1997

[54] GAMMA CAMERA WITH ON THE FLY CALIBRATION FOR PMT DRIFT

[75] Inventor: David S. Vickers, Independence, Ohio

[73] Assignee: SMV America

[21] Appl. No.: 666,146

[22] Filed: Jun. 19, 1996

[51] Int. Cl.⁶ .................................................... G01T 1/208
[52] U.S. Cl. .................... 250/363.09; 250/252.1
[58] Field of Search .................... 250/363.09, 363.07, 250/252.1

[56] References Cited

U.S. PATENT DOCUMENTS

| | | |
|---|---|---|
| 4,272,677 | 6/1981 | Berthold et al. . |
| 4,857,722 | 8/1989 | Kumagawa et al. ............... 250/363.09 |
| 4,866,615 | 9/1989 | Ichihara . |
| 5,004,904 | 4/1991 | Yamakawa et al. . |
| 5,373,161 | 12/1994 | Tararine et al. . |
| 5,410,153 | 4/1995 | Ferreira . |
| 5,449,897 | 9/1995 | Bertelsen et al. . |
| 5,512,755 | 4/1996 | Vickers et al. . |
| 5,539,202 | 7/1996 | Geagan et al. . |

FOREIGN PATENT DOCUMENTS

| | | |
|---|---|---|
| 0066763 | 5/1982 | European Pat. Off. . |

OTHER PUBLICATIONS

*Photomultiplier Handbook*, by Burle Technologies, Inc., 1980, pp. 80–83 and 126–127.

*Primary Examiner*—David P. Porta
*Assistant Examiner*—Richard Hanig
*Attorney, Agent, or Firm*—Frank J. Nawalanic

[57] ABSTRACT

An automatic calibration system corrects for photomultiplier drift while the gamma camera is in imaging mode. The known constant energy from the gamma rays producing scintillated light is used to effect the drift adjustment by weighting the position signals of the scintillations to determine if a valid event has occurred and building, for each photomultiplier in the camera, a statistically valid, spectral energy histogram. When the histogram counts reach a sufficient sample size the histogram data is read out in a discriminatory manner to account for noise and Compton scattering effects and used to either directly adjust the photomultiplier gain or the calibration look up tables depending on what type of system is used by the camera to process the photomultiplier signals.

27 Claims, 6 Drawing Sheets

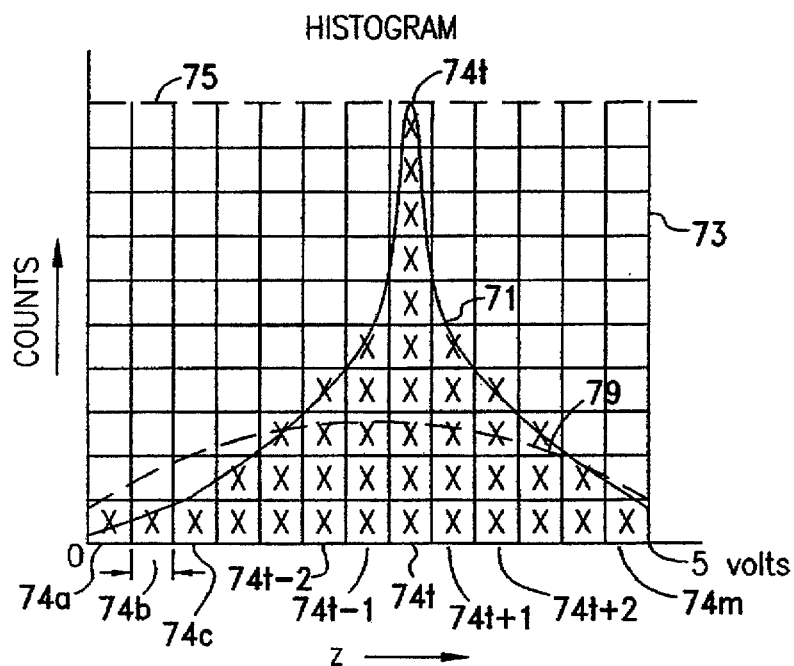
Fig. 6
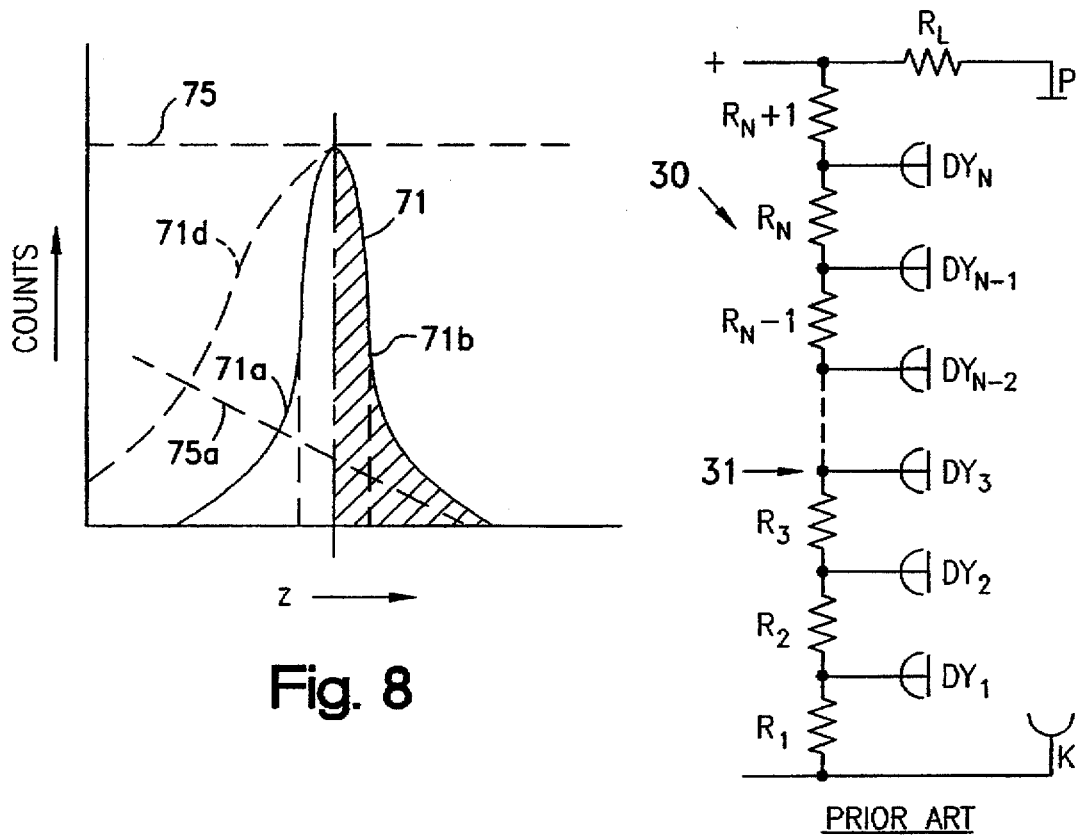
Fig. 8
Fig. 4 PRIOR ART

GAMMA CAMERA WITH ON THE FLY CALIBRATION FOR PMT DRIFT

FIELD OF THE INVENTION

This invention relates generally to gamma cameras and more particularly to a method and apparatus for calibrating the camera during camera operation.

The invention is particularly applicable to and will be described with specific reference to an arrangement for automatically calibrating the photomultipliers of a gamma camera even while the camera is in an imaging mode to compensate for photomultiplier drift. However, the invention may have broader application, and in a sense, may be utilized to adjust any type of radiation detector while the detectors are in a sensing mode.

INCORPORATION BY REFERENCE

My U.S. Pat. No. 5,512,755, dated Apr. 30, 1996, entitled "Gamma Camera Device" is incorporated by reference and made a part hereof. This invention may be viewed as an improvement to the invention disclosed in my '755 patent.

In addition the following patents are incorporated by reference so that details relating to gamma cameras and imaging techniques known in the art need not be repeated herein:

U.S. Pat. No. 4,272,677 to Berthold et al., dated Jun. 9, 1981, entitled "Method and Apparatus for the Automatic Stabilization of Drift in Radiation Measurements";

U.S. Pat. No. 4,866,615 to Ichihara, dated Sep. 12, 1989, entitled "Scintillation Camera Compensation for Shifting the Center Channel of the Energy Spectrum Due to Photomultiplier Gain Change";

U.S. Pat. No. 5,373,161 to Tararine et al., dated Dec. 13, 1994, entitled "Gamma Camera with Gain Compensation";

U.S. Pat. No. 5,410,153 to Ferreira, dated Apr. 25, 1995, entitled "Position Calculation in a Scintillation Camera"; and U.S. Pat. No. 5,449,897 to Bertelsen et al., dated Sep. 12, 1995, entitled "Automatic Gain Calibration for Gamma Camera System".

None of the patents incorporated by reference herein form any part of the present invention.

BACKGROUND OF THE INVENTION

The gamma-ray camera, originally developed by H. O. Anger, is a sophisticated scintillation counter used in the medical field for locating tumors or other biological abnormalities. A radioactive isotope combined with a suitable compound is injected into the blood stream or taken orally. Certain body organs take up the compound and as the isotope disintegrates, gamma rays are emitted. Those rays are sensed by the gamma camera and an image, two or three dimensional (computed) is developed.

All gamma cameras include a lead collimator through which gamma rays are passed so that only those rays parallel to the slits in the collimator strike a scintillation crystal. The light of individual scintillations emanating from the scintillation crystal is not collimated but spreads out and travels through light tubes or fiber optics to strike a plurality of photomultipliers (hereinafter "PMT") which usually have face plates arranged in a close fitting hexagonal matrix. The location of the point of scintillation origin is then obtained by algorithms based on a weighted average, typically, of all the individual signals from the photomultipliers.

Specifically, the electrons or signals produced in the PMTs in response to the photons detected are essentially counted in pulses. Each pulse is formed into an intensity signal, z, which is correlated to the energy of the sensed photon(s) and a position signal, x,y, tied to the PMT where the signal originated. Various techniques are then used to produce a scintillation signal. Typically, each signal is adjusted through a compensation circuit which factors each PMT's z signal by the gain of the PMTs previously established and stored in look up tables during camera calibration for that particular isotope being imaged. After adjustment for PMT gain (correlated to the imaged isotope), all the signals are typically weighted (summed and averaged) to determine the intensity or spectral energy or z component at a calculated x,y position when any one of the PMTs produces a z intensity signal beyond a pre set limit which establishes that that particular PMT detected a scintillation event. The scintillation event signal is then adjusted for the uniformity, linearity, and energy and stored in memory which is accessed to produce a scintillation image.

Obviously, the look up tables established during camera calibration and used in the compensation circuit have to be accurately and precisely established in the first instance. Typically, calibration occurs by fitting an aperture mask over the detecting heads and then placing a known quantity of a specific radioactive isotope between the heads to generate a uniform flood of radiation which each PMT sees. Various iterative techniques coupled with manual adjustments of PMT line voltages (or divider string voltages) are then effected to develop a look up table which is supposed to produce, for each PMT, an identical intensity signal. In this connection my prior invention set forth in U.S. Pat. No. 5,512,755, disclosed an automatic control in which the dynode voltage for each PMT was automatically controlled during calibration to set the gain for each PMT so that the output signal of each PMT was identical to one another. The computer stored the gain voltages and automatically set the gain for each PMT once the operator identified to the computer which isotope was to be imaged. The '755 invention, among other things, i) eliminated the compensation circuit, ii) produced a better PMT signal by individually and physically adjusting each signal (thus insuring each PMT operated in its linear output mode) and iii) provided a better calibration for all PMTs since automatically adjusting each PMT produced uniform PMT output with few iterations. This invention utilizes my prior invention in that the PMTs are likewise physically controlled on an individual basis to produce a desired output. However, the invention is improved because of the method and apparatus, disclosed herein, in which each PMT's gain is established for any particular isotope.

Once the camera has been calibrated for all the isotopes, it is known that the output signals from the photomultipliers will gradually change or drift as a function of time or use. Eventually the drift, which is cumulative, distorts the output such that the camera has to again be recalibrated. While the calibration with my prior invention is automatic, a technician is still required to set the flood fields for all the isotopes and the camera is down for about 30 to 60 minutes while the computer automatically sets the gain for a specific isotope. When a typical gamma camera must be able to image well over 20 different isotopes, calibration downtime becomes significant and somewhat expensive.

The prior art has recognized the photomultiplier drift problem for some time and almost all commercial gamma cameras now sold on the market have some mechanism for automatically correcting for photomultiplier drift while the camera is imaging or "on the fly" so to speak. The technique most widely used, believed originally developed by General Electric, is to place LEDs at the edges of the PMTs or in PMT groupings and pulse the LEDs to produce light scintillations of known energy. The signal produced by the photomultipliers during the LED light pulses is then compared to what the known value should be for the pulsed LED light and the gain look up table adjusted accordingly. Reference can be had to U.S. Pat. Nos. 4,272,677; 5,373,161 and 5,410,153 for further explanation of several light pulsing techniques. While this technology is tried and proven, there is an obvious cost involved in equipping the PMTs with LEDs and the associated circuitry required to discriminate between LED scintillations and gamma event scintillations. Inherently in this technique, a wait is required for the LED flash to dissipate itself before the gamma camera is ready to record a gamma event. Cumulatively, this wait produces an inefficiency in the camera. The problem is discussed at length in U.S. Pat. No. 5,373,161.

Another method for continuously adjusting for drift of the photomultipliers which is perhaps more pertinent to this invention is discussed in the Background section of the 5,373,161 patent and a disclosure of an arrangement where the gamma radiation itself is used to correct for PMT drift is disclosed in U.S. Pat. No. 4,866,615. In the '615 patent a conventional arrangement is shown in that the PMT signals are all read out and then adjusted for position and energy by look up tables in a compensation circuit after which the adjusted signals are then "windowed" to determine if a scintillation event has occurred and for those signals which have exceeded a set energy level, the data is transferred to memory for scintigram construction. To account for drift, the PMT signals, within a preselected sampling range, have energy readings stored in energy range channels of an energy analyzer. A shift in the peak channel position, in turn, correlated to an x,y position, results in the look up table being changed. While the reference is relevant in that the light from the gamma radiation to produce imaging is also used to adjust for PMT drift, the sampling technique is believed neither accurate nor reliably consistent. For example, no attempt is made to distinguish the noise induced component of the stored signal resulting in erroneous samples being taken. More significantly, the signals stored in the channels are not weighted nor sampled to account for light from adjacent PMTs. Thus, an accurate spectral energy at a fixed position can not be obtained. In addition the technique cannot account for dual isotope imaging where more than one peak is generated. Further, the technique disclosed uses a calibration table downstream of the PMTs to adjust the gain or intensity readings of the PMTs. As discussed above, should any particular PMTs have drifted into a non-linear signal output range, repeated corrections will be likely which eventually will result in camera instability requiring recalibration, a fact that the '615 patent notes will eventually occur. Finally, the technique cannot develop accurate energies permitting the camera to be initially calibrated. Only adjustments to a calibrated camera are possible.

Another reference, U.S. Pat. No. 5,449,897, discloses an arrangement which permits initial calibration of the gamma camera with the collimator in place which is not particularly pertinent to this invention. However, the '897 patent discloses continuously correcting the baseline voltage applied to the PMTs which baseline voltage is said to drift because of changes in the electronics or the PMTs. Should the baseline voltage go negative, inaccurate PMTs readings will occur. Those skilled in the art know that the baseline voltage may be conventionally used to set the gain of the PMTs (although a far better control of gain is obtained by setting a specific dynode voltage). While the gain is not specifically set by the disclosed technique (which is accomplished by look up tables downstream of the PMT signal), the PMTs are continuously adjusted to insure a positive PMT signal. The disclosed technique samples the baseline voltage for the PMTs not receiving a scintillation event (whether the camera is imaging or not) and builds a histogram which is then read to determine if a drift has occurred and the baseline voltage adjusted. In general terms the reference, like U.S. Pat. No. 4,866,615, discloses the gathering of data driven by an event occurring during the operation of the camera which event is sampled to adjust the baseline voltage of the detector heads of a gamma camera to prevent the PMT voltage going negative.

SUMMARY OF THE INVENTION

Accordingly, it is a principal object of the invention to provide a system (method and apparatus) which utilizes only the scintillated light generated from detected gamma events to collect a sufficient quantity of data which can be sampled in a statistically valid manner to ascertain and adjust the gain of the PMTs.

This object along with other features of the invention is achieved in a method for individually adjusting the gain of the PMTs in a gamma camera operated in a conventional manner in that for any given PMT, a triggering PMT, which detects a scintillation event (one which produces a signal above a set limit) there is triggered a grouping or clustering of a selected plurality of PMTs associated with the triggering PMT and the triggering PMT's signal along with the clustered PMTs' signals are individually digitized into a set of grouped signals, (each signal having an x,y position component and a z spectral energy component) which are weighted to produce a single digitized scintillation event signal that conventionally corresponds to a pixel of a scintillation image. The method broadly includes the steps of a) providing a multi-channel analyzer for each PMT with each channel of each analyzer assigned a specific range of spectral energies; b) counting the z component of the scintillation event signal into the channel of the triggering PMT's analyzer whose range encompasses the z component of the scintillation event signal provided that the x,y position component of the scintillation event signal is within a set distance from the center of the face of the triggering PMT; c) calculating and reading out the peak z energy recorded in the triggering PMT's multi-channel analyzer when the number of scintillation event signals stored in that analyzer reaches a set number; and, d) using the peak z energy thus read out from the triggering PMT's multi-channel analyzer to set the gain of that specific triggering PMT whereby upon repeating the method steps for all the camera's PMTs (which eventually and repeatedly become triggering PMTs), the camera is calibrated for any specific radioactive isotope.

In accordance with another general feature of the invention, the peak spectral energy sampled, read out and analyzed from a triggering PMT's multi-channel analyzer is used to set the gain of that specific triggering PMT by either i) adjusting the voltage potential of a specific dynode for the triggering PMT (which is preferred) or ii) adjusting the gain amplification circuit for the triggering PMT or iii) rewriting the stored spectral energy value for the triggering PMT in a calibration look up table which conventionally modifies the spectral energy signal components of the PMTs prior to weighting the PMTs to develop a scintillation event signal whereby the calibration system of the invention can be applied to any conventional camera system.

In accordance with another unique feature of the invention, the peak z energy obtained in step (c) is compared to a z energy previously stored for the triggering PMT so that when a difference beyond a set amount between the two signal components is detected, the gain of the triggering PMT is set to that recorded in the triggering PMT's multi-channel analyzer whereby the system not only is used to initially calibrate the camera but is also used to continuously adjust the camera for PMT drift, including electronic drift, while the camera is in its normal, operating imaging mode.

In accordance with another important aspect of the invention, when any triggering PMT's multi-channel analyzer is read out, that specific multi-channel analyzer is re-set to zero and the method continued so that when one specific triggering PMT's histogram has reached a sufficient number of counts in step (b) to be read out as in step (c), the remaining multi-channel histograms continue to accumulate data whereby the method not only automatically adjusts the PMTs but the method is self correcting in that the effect of a gain adjustment during imaging for any specific triggering PMT becomes weighted and statistically accounted for in the histograms developed and being developed after the adjustment is made, thus accounting for any change induced in those PMTs adjacent to and attributed to an adjusted triggering PMT.

In accordance with another specific feature of the invention, step (c) further includes the steps of i) determining if any channel, a triggering channel, in the multi-channel analyzer reaches a set number of counts and then ii) determining if either one of the two channels adjacent the triggering channel has stored therein a number of counts or scintillation events which equal at most 70% of the counts recorded in the triggering channel before determining that the multi-channel's peak z component is valid so that not only is the histogram developed in the multi-channel analyzer based on a sufficient data size which can be statistically sampled in a valid manner but also a discriminatory step is provided to detect the presence of noise and other unwanted effects which could otherwise distort or corrupt the multi-channel analyzer signal. Still further, the peak z component is determined by weighting the number of counts in the triggering channel with that of adjacent channels to arrive at a precise peak z component value notwithstanding the fact that each channel has a range of energy associated therewith.

Still yet in accordance with a particularly significant feature of the invention, it was discovered that the histogram accurately reflected spectral energies of the gamma radiation attributed to Compton scattering which, if present, are not considered in determining the peak spectral energy of the histogram so that the patient's degree of corpulence does not affect the system's ability to calibrate the camera.

In accordance with the apparatus feature of the invention, an improvement is provided in a gamma camera which includes a first plurality of PMTs, each PMT generating analogue signals in response to scintillations produced by gamma rays and the camera having a detection mechanism triggered, when any given PMT, a triggering PMT, generates an analogue signal above a set limit indicative of a scintillation event. A multiplexer clusters or groups analogue signals from a smaller second plurality of PMTs within the first plurality and generally adjacent the triggering PMT to define along with triggering PMT's analogue signal, a clustered group of PMT analogue signals. An analogue to digital converter converts each PMT analogue signal in the cluster group into a digital signal having an x,y position component and a spectral energy z component and a weighting table factors the clustered group of digital signals to produce a single digital scintillation event signal used to develop a pixel in a scintigram. The improvement includes a) each PMT having a corresponding multi-channel analyzer with each analyzer having a plurality of channels, each channel divided into set ranges of spectral energies; b) a digital signal processor for counting the scintillation event signal into the channel corresponding to the intensity thereof for the triggering PMT's multi-channel analyzer when the x,y position component of the scintillation event signal is within a set distance from the center of the triggering PMT; c) the digital signal processor further includes a readout mechanism for recording the peak spectral energy within the triggering PMT's multi-channel analyzer when the number of events or counts stored therein have reached a set number, and d) a comparison mechanism which compares the peak z component of the read out multi-channel analyzer with the previously stored z component associated with the triggering PMT whereby the gain of the triggering PMT is adjusted if the difference between the z components exceeds a set value.

It is thus an object of the invention to provide a system which automatically corrects the gamma camera for PMT drift (as well as electronic drift) without the use of external light sources of any type, pulsed or non-pulsed.

It is another object of the invention to provide a system for use in the gamma camera which automatically corrects any individual PMT which may have drifted by adjusting the gain of any drifted PMT so that the PMT continues to produce a linear output signal in response to a scintillation event while the other PMTs continue to operate pursuant to their preset gain.

It is yet another object of the invention to provide a system for use in the gamma camera which automatically corrects the camera for photomultiplier drift without causing any delay in the imaging process or degradation in the scintillations produced by the camera.

Yet another object of the invention is to provide a system for use in the gamma camera which, for each PMT, develops histograms of only valid scintillation events which are sampled in a statistically valid, discriminatory manner to produce accurate PMT gain adjustments.

Still another important object of the invention is to provide a system which initially calibrates a gamma camera for any specific radioactive isotope in a completely automatic, self-correcting, iterative manner.

Still another important object of the invention is to provide a system which not only initially calibrates the camera but also automatically recalibrates the camera during imaging.

Still another object of the invention is to provide a system for calibrating and recalibrating the camera which can be applied to any conventional gamma camera.

Still yet another object of the invention is to provide a system which can automatically recalibrate a gamma camera while the camera is performing dual isotope imaging.

A still further object of the invention is to provide a system without external light sources for automatically calibrating a gamma camera while a patient is being imaged and which is not adversely influenced by radiation attributed to Compton scattering.

Yet another object of the invention is to provide a gamma camera which has provisions for automatically calibrating and recalibrating the camera to account for photomultiplier drift which provisions am simple, inexpensive, and easily retrofitted to existing gamma cameras.

As used herein, "system" in relation to a gamma camera means apparatus making up the gamma camera components which control the gain of the PMTs and/or "method" means the operation of the gamma camera or the PMT gain control portion of the gamma camera.

These and other objects and features or advantages of the present invention will become apparent to those skilled in the art upon reading and understanding the Detailed Description of the invention set forth below.

BRIEF DESCRIPTION OF THE DRAWINGS

The invention may take form in certain parts and arrangement of parts, a preferred embodiment of which will be described in detail and illustrated in the accompanying drawings which form a part hereof and wherein:

FIG. 4 is a schematic representation of a voltage divider resistance string typically employed in PMTs and is prior art;

FIG. 6 is a representation of a histogram developed by a multi-channel analyzer used in the invention;

FIG. 8 is a graphical representation of a histogram signal developed by a multi-channel analyzer used in the invention with and without Compton scattering;

DETAILED DESCRIPTION OF THE INVENTION

Figure 1:
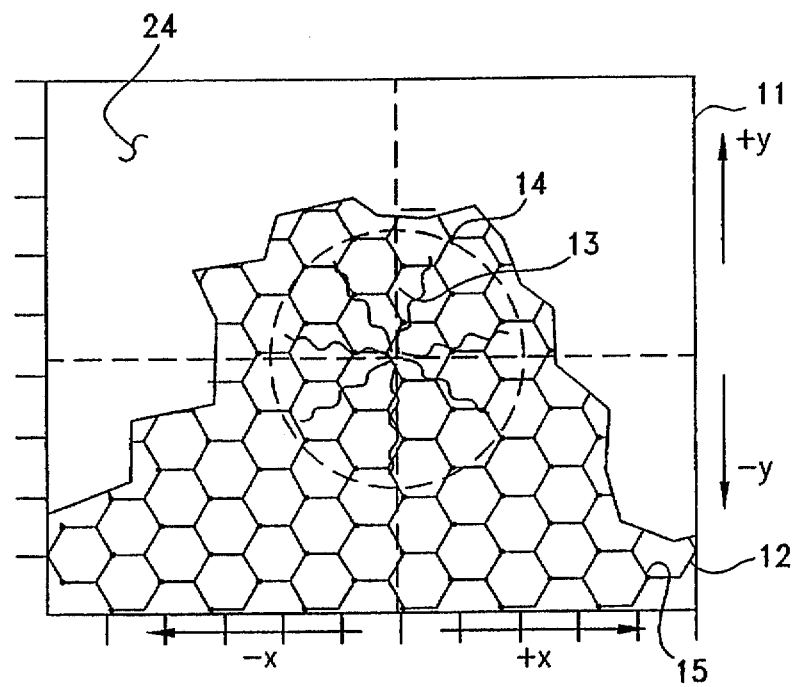
FIG. 1 is a diagrammatic, plan view of one of the detector heads of a gamma camera illustrating the PMT matrix with the gamma ray representation superimposed thereon and is prior art.

Referring now to the drawings wherein the showings are for the purpose of illustrating a preferred embodiment of the invention only and not for the purpose of limiting same, there is shown in FIG. 1 schematically, a detector head 11 of a gamma camera with a section broken away to show a matrix of photomultipliers or PMTs 12.

As is known in the art, PMTs 12 emit photoelectrons from a scintillated burst of light which are created by the photocathode and are directed by an appropriate electric field to an electrode or dynode which, in turn, emits a greater number of secondary electrons directed to the next dynode, etc., until a high gain of electrons are collected by the anode which provides a signal outward current correlated to the incident rate of radiation. "Gain" as used in this specification will have the meaning ascribed it as set forth in the *Photomultiplier Handbook* (Burle Industries, Inc., Copyright 1980, p. 126), namely, "the ratio of (1) the output signal current to (2) the photoelectric signal current from the photocathode". Also, "gamma ray" as used or claimed herein includes photons produced by positron annihilation. "Gamma camera" includes a camera capable of performing single photon emission computer tomography (SPECT), as well as positron emission tomography (PET), as well as developing conventional scintillation images or scintigrams.

Referring still to FIG. 1, which is prior art, and as is well known, a gamma ray indicated schematically at reference numeral 13 having a known energy determined by the particular radioactive isotope administered to the patient strikes the scintillation crystal and produces light beams of a given energy or intensity which spread out and pass by light guides to impinge upon the face of a plurality of PMTs 12. The intensity signal developed by PMTs 12 is a function of the energy of gamma ray 13 and the distance the scintillation travels until striking the face of any particular PMT 12. In the conventional prior art gamma camera, each PMT's electrical signal in the matrix is read out and assigned an x,y position and the entire matrix string of signals are summed and averaged by position and intensity to identify the position on detector head 11 where the scintillation event occurred. The scintillation frequencies are then stored at their appropriate address or positions in memory and read out to construct pixels making up the scintillation image. As generally illustrated in FIG. 1, the scintillations produced by gamma ray 13 impact a number of PMTs 12 in an area circumscribing the point at which gamma ray 13 initially contacted the scintillation crystal as indicated generally by dash-line 14. PMT's 12 outside area 14 do not see the scintillation caused by the gamma event but do generate signals attributed to noise and other stray influences. Such signals are nevertheless weighted in and thus included in the data used to calculate the center and intensity of the gamma ray event. In this invention, a clustering technique, which has been recently adopted by several other gamma manufacturers, is employed in which PMT signals within a defined area such as indicated by dash-line 14 are sampled and weighted to determine the incident position and intensity of gamma ray 13 with a far greater accuracy than that produced in conventional gamma cameras, which, in turn, improves camera resolution, etc.

As discussed in the Background section above, it is known that the output signals from PMTs 12 will vary or drift as the PMTs (as well as the associated electronic circuitry) age for any number of reasons. The drift is typically very slow but it is cumulative and eventually image resolution is adversely affected requiring complete calibration of the camera. The prior art has recognized this problem and has proposed various techniques to adjust the camera for PMT drift while it is being used. The technique believed most widely used in the industry is to place light sources, typically LEDs 15, at the edges of PMTs 12. LEDs 15 produce a constant source of light at a known energy spectra which functions as a baseline light source against which the PMTs can be adjusted for drift. More particularly, LEDs 15 are pulsed and the output signal generated from PMTs 12 generated during the pulsations compared to what they previously were and PMT gain adjusted accordingly. However, the scintillations produced by LED pulses have to, or should, die out before the scintillations produced by gamma rays 13 can be accurately recorded by PMTs 12. Various techniques have been proposed to remove or dissipate any interference between the scintillations caused from the pulsing LEDs and the detection of gamma ray scintillations. For example, LEDs 15 have been pulsed only in areas remote from the scintillation event.

Figure 3:
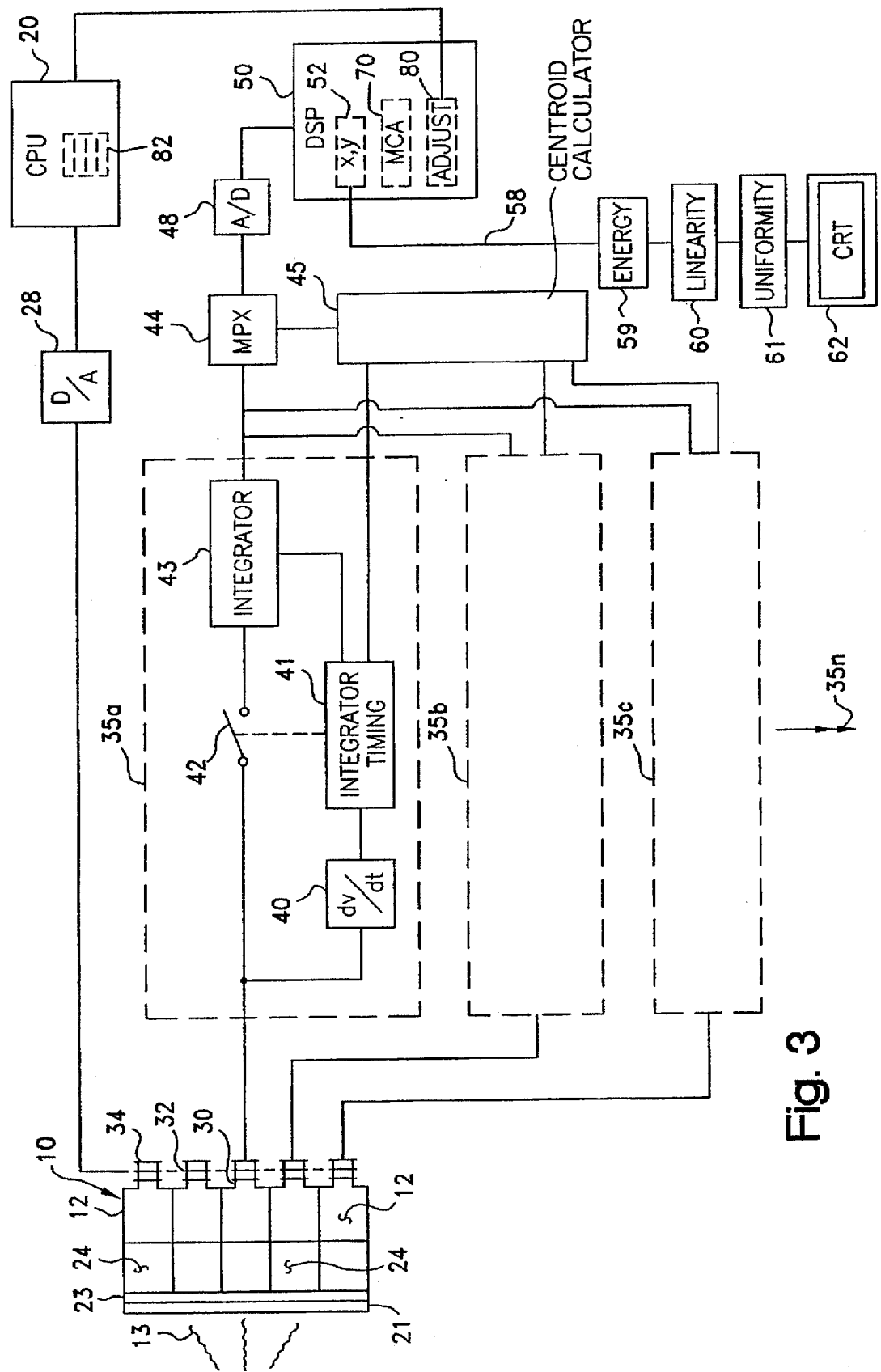
FIG. 3 is a general, schematic diagram, in block form, of a gamma camera with the present invention.

Referring now to FIG. 3, there is shown in schematic form a nuclear camera 10 of the Anger type. Camera 10 includes a lead collimator 21 for catching and directing certain parallel incident rays of radiation 13 onto a scintillation crystal 23. Scintillation crystal 23, in turn, produces as a result of absorbing a ray of radiation 13, a burst of light which is directed by light tubes 24 onto the photocathode of a plurality of PMTs 12 (photomultiplier tubes).

Reference can now be had to my prior U.S. Pat. No. 5,512,755, incorporated by reference and made a part hereof, for a description of the gain control used in the preferred embodiment in this invention for each PMT 12. For purposes of this invention, it is believed sufficient to simply identify the functional features of the circuits disclosed in my '755 patent which allow a central computer 20 to set the gain for each individual PMT 12 in camera 10. Briefly, a voltage driver or divider circuit 30 making contact with the photocathode, anodes and dynodes of PMT 12 controls the voltage potential of a given dynode in PMT 12 to establish the gain of PMT 12. A general PMT voltage divider circuit 30, in fact, one taken from *Photomultiplier Handbook*, is illustrated in FIG. 4. In accordance with my prior invention, a voltage potential established by central computer 20 on bus 31 sets the potential for a given dynode, dynode 3 in FIG. 4, to establish the gain of PMT 12 to, in turn, produce an intensity signal within the linear output range of PMT 12 correlated to the spectral energy of gamma ray 13. Specifically, a gain control circuit 32 receiving commands from computer 20 sets the voltage potential on line 31 for a specific dynode to control the PMT gain. Finally, a somewhat conventional preamp circuit 34 amplifies the analogue signal outputted from voltage divider circuit 30. Thus, the gain of each PMT 12 is physically adjusted automatically by computer 20. Physically controlling the gain at each PMT 12 on an individual PMT basis provides a number of advantages discussed in my '755 patent and thus not repeated again herein. Referring still to FIG. 3, it should be noted that the general schematic for camera 10 does not employ any conventional calibration or compensation look up table downstream of the analogue to digital converter because the function of such tables have been replaced by the automatic, physical adjustment to each PMT 12 thus described.

In camera 10 of the preferred embodiment, scintillation crystal 23 is rectangular (about 20 inches×26 inches) and PMTs 12 have hexagonal face plates and are packed in a hexagonal array of 58 tubes. Each PMT 12 has its own event detection circuit, shown by dash line envelope 35 in FIG. 3, to determine when that specific PMT 12 has detected a scintillation event. In the preferred embodiment, there are 58 event detection circuits 35. The detection of a scintillation event is determined, in the preferred embodiment, by a dv/dt circuit 40. Dv/dt circuit 40 senses the rate of change in the voltage produced by the corresponding PMT 12 to determine if a scintillation event has occurred. "Scintillation event" as used herein and in the claims means the scintillation produced at the incident contact point of gamma ray 13 with scintillation crystal 23. (A conventional maximum voltage sensing circuit could be used in place of dv/dt circuit 40 to determine when a scintillation event has occurred.) When dv/dt circuit 40 senses a scintillation event, an integrator timing circuit 41 is actuated. Integrated timing circuit 41, in turn actuates, in effect, a "switch" 42 which momentarily establishes contact with an integrator 43 before opening. Integrator timing circuit 41 also controls the time during which integrator 43 integrates the PMT's analogue signal to produce an intensity or spectral energy or z component signal which is sent to a multiplexor 44. Integrator timing circuit 41 also inputs to the motherboard or centroid calculator 45 the fact that dv/dt circuit 40 has detected a scintillation event for a specific PMT 12. Centroid calculator 45 then determines, for that specific PMT which detected a scintillation event, a grouping or clustering of PMTs (i.e., within area 14) and for each PMT 12 within the cluster, centroid calculator 45 causes integrator timing circuit 41 to close switch 42 so that integrator 43 can integrate the intensity signal of each PMT within the cluster. In the preferred embodiment, 18 PMTs 12 adjacent that PMT which detected the scintillation event (i.e., a total of 19), are grouped or clustered and their analogue signals are multiplexed by multiplexor 44 under control of centroid calculator 45 to, in turn, generate a string of 19 PMT analogue signals, each having an intensity or spectral energy component z and an address or x,y position component corresponding to the center of each PMT within detector head 11. The cluster string of 19 signals are then digitized in an analogue to digital convertor 48 and the clustered digitized signals are inputted to digital signal processor 50.

Within digital signal processor 50 is a weighting table 52 which sums, weights, and averages the clustered group of signals to develop a scintillation event digitized signal having a calculated x,y position component and a calculated z component. The weighting calculation is conventional and is expressed by the following formula:

$$z = \Sigma_i E_i$$

$$x = \frac{\Sigma_i W_{xi} E_i}{Z}$$

$$y = \frac{\Sigma_i W_{yi} E_i}{Z}$$

where $W_x$=weight at the specified x PMT coordinate
$W_y$=weight at the specified y PMT coordinate
$E_i$=the integrated pulse signal
$\Sigma_i$=1 ... 19

Referring still to FIG. 3, the weighted scintillation event signal is outputted from x,y table 52 on bus 58 where it is corrected through software for i) imagery distortion by an energy distortion correction 59, ii) linearity through a linearity correction 60 and, iii) uniformity through a uniformity correction 61. The reformed radiation signal is then eventually inputted to a cathode ray tube 62 where each signal forms pixels of various shades which make up the scintigram. As thus far described, camera 10 is conventional. Because the system is conventional, details of the circuits shown in the system are not described. Further, it is believed sufficient, given the level of expertise of one skilled in the gamma camera art, to specify the functional relationship of the components in the system as set forth above. One skilled in the art, from known circuitry and techniques readily known in the art, can construct the appropriate timing circuits, integrators, etc. required by the system.

Figure 2:
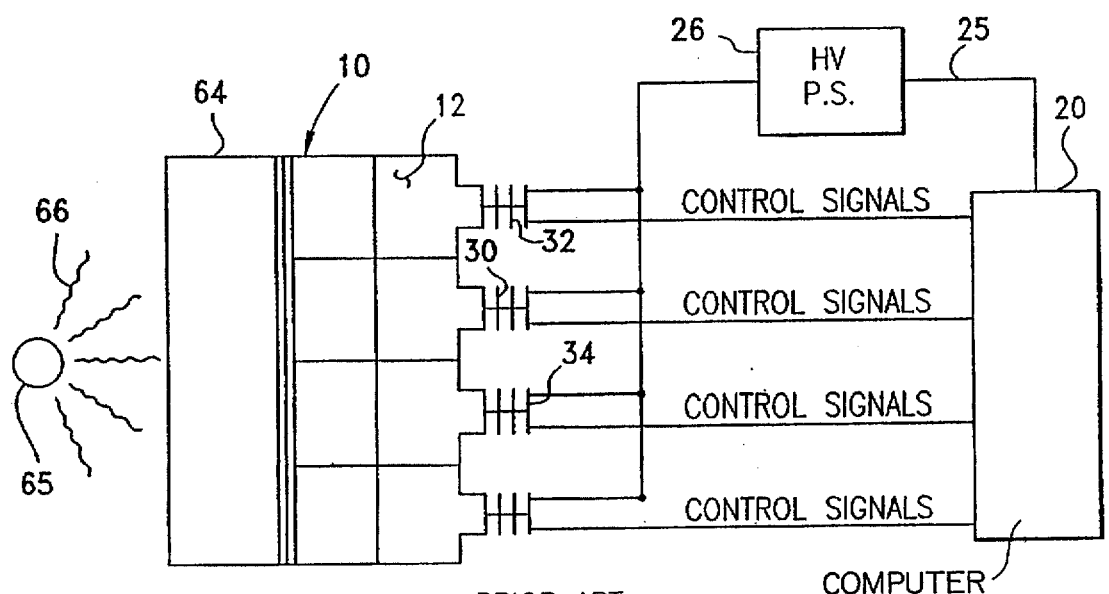
FIG. 2 is a block form schematic of the mechanism used to initially calibrate the gamma camera and is prior art.

Referring now to FIG. 2 (which is a substantial copy of FIG. 9 of my '755 patent) there is shown a general schematic illustrating how the gain for each PMT 12 was set using the conventional camera 10 described thus far with my prior invention. In FIG. 2, gamma camera 10 is fitted with a conventional lead aperture mask 64 for calibration. In front of mask 64 is placed a specific radioactive isotope 65 which is situated, sized, etc. to produce a uniform flood of gamma test rays 66 so that each PMT 12 receives the same radiation. Accordingly, each PMT 12, if identical with one another, would develop the same output gain signal. This does not occur for any number of reasons. Accordingly, calibration occurs generally as follows. For each test isotope, computer 20 has stored an optimum high voltage for voltage divider circuit 30 which was calculated to give maximum gain but well within the linearity range of PMT 12. This stored command is outputted on bus 25 to a high voltage power supply 26 which makes sure the PMT base line voltage does not go negative. This high voltage signal is sent to divider circuit 30 as shown for each PMT 12. The output gain signals for each PMT 12 are inputted from preamp circuit board 34 to computer 20. At this point, each PMT 12 is at maximum gain. The output gain signals are then compared and a PMT gain signal is developed by computer 20 to reduce the gain of all PMTs 12 to be identical to that of the least responsive PMT 12 in the array. This is accomplished by utilizing the gain/dynode N voltage function (known to those skilled in the art). Computer 20 is now ready to output a specific PMT gain signal to gain circuit board 32 for each PMT 12 for that isotope. The computer stores PMT gain signals in a look up table for that particular isotope and the entire process is repeated for the next isotope. The calibration process is automatic once the isotope is placed in front of lead mask 64. When camera 10 is operated the technician simply identifies to computer 20 the specific radioactive isotope injected or ingested by the patient and the gain adjustment is automatically accomplished by computer 20.

Figure 5:
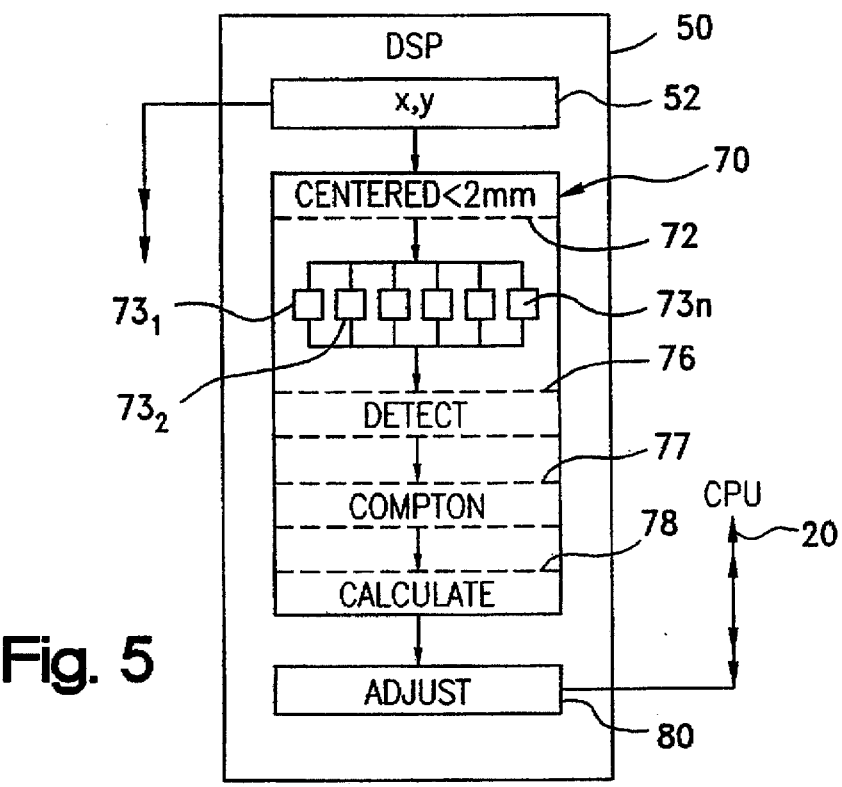
FIG. 5 is an enlarged view of the digital signal processor used in the invention and shown in FIG. 3.

Referring now to FIGS. 3 and 5, digital signal processor 50 is a conventional signal processor having conventional ROM for storing values, look up tables, formulas, etc. and RAM for performing programmed functions and is not described for the routines programmed in digital signal processor 50 since they are believed apparent to those skilled in the art. Within digital signal processor 50 is a histogram program 70 and an adjust program 80 as well as weighting table 52.

Within histogram program 70 is a center routine 72 which has stored the center face positions of each PMT in the detector head matrix, i.e., 58 x,y positions for the preferred embodiment. The identity of the specific PMT 12 (and hence its centered x,y face position) which triggered event detector 35 is, of course, known and is hereafter referred to as the triggering PMT. The x,y position component of the scintillation event signal (i.e., the signal developed at weighting table 52) is compared to the triggering PMT's center distance in center routine 72. If the scintillation event signal is within a set distance of the triggering PMT's center, the event is counted. If the scintillation event signal is not within the set distance, the event is simply discarded (although used, of course, to form the scintillation image as previously described) and histogram program 70 waits for the next scintillation event signal to process. The set distance is empirically determined and depends on a number of factors including the cluster size, the size of the face detection surfaces of the PMTs, etc. For the preferred embodiment, a distance of 2 mm has been determined to give reliable data at a count frequency sufficient to permit calibration of the entire array within a time of about 10 to 15 minutes. It has been determined that this distance could be expanded to a distance of 4 mm and the invention will still record valid events. Also, those skilled in the art will recognize that a weighted, accurate signal is being compared to a centered PMT position to produce a valid event. The center is the optimal position. However, it is within the scope of the invention that a position or discrete area off center could be utilized. (In fact, each PMT could have several multi-channel analyzers associated therewith. For example, one centered and several off-centered and the process would, in all probability speed up but not that significantly.) The preferred embodiment uses only the centered position of each PMT.

If a valid scintillation event has been detected by center routine 72, the event is read into a buffer or multi-channel analyzer 73 assigned to that triggering PMT. Specifically, each PMT 12 has a specific multi-channel analyzer 73 assigned to it. Thus, digital signal processor 50 has multi-channel analyzer $73_1 \ldots 73_n$ (as shown in FIG. 5) and when center routine 72 determines a scintillation event is "valid", the event is read into that triggering PMT's multi-channel analyzer $73n$. In the preferred embodiment, there are 58 multi-channel analyzers 73.

Referring now to FIGS. 5 and 6, each multi-channel analyzer 73 has a plurality of bins or channels 74 with each channel set for a discrete spectral energy range in ascending order. In the preferred embodiment, 16 channels are used, with each channel having a spectral energy range of 0.3125 volts over an energy spectrum extending from 0 to 5 volts. The z component of the digitized scintillation event signal is counted as an event in that channel 74 of multi-channel analyzer 73 having a spectral energy range within which the scintillation event's z component falls. The specific multi-channel analyzer 73 which is being accessed is, of course, the multi-channel analyzer assigned to the triggering PMT. The next scintillation event detected by camera 10, if valid, likewise gets counted in the appropriate channel of that triggering PMT's multi-channel analyzer 73 and so on. In a somewhat surprising short time, histograms 71, as shown in FIG. 6 begin to develop for all PMTs in the matrix.

Within histogram program 70 is a detector program routine 76, a Compton program routine 77 and a calculate program routine 78 which collectively determine first, if the data stored in histogram 71 is valid and then reads out a precise spectral energy value. Detector routine 76 determines when any one channel, a triggering channel $74t$, reaches a preset maximum number of counts indicated by a maximum count line 75 in FIG. 6. Detector routine 76 then reads the number of counts or events stored in the channel on either side of triggering channel $74t$, i.e., $74_{t+1}$ and $74_{t-1}$. If either one of these two channels, $74_{t+1}$ and $74_{t-1}$ has a count number which, in the preferred embodiment, is not more than 70 percent of the number of counts in triggering channel $74_t$, the triggering multi-channel analyzer is read out to Compton routine 77 and calculate routine 78. While the preferred embodiment is set to determine that the event is valid when the number of counts in an adjacent channel is not more than 70% of the counts in the peak channel, a higher percentage could be utilized. Specifically, it is believed that a statistically valid discrimination will occur if either one of the number of counts in the adjacent channels $74_{t+1}$ or $74_{t-1}$ is not more than 80% of the number of counts in triggering channel $74_t$. Consistent with terminology employed throughout, when a channel 74 becomes a triggering channel $74_t$, the multi-channel analyzer becomes a triggering multi-channel analyzer $73_t$.

In the preferred embodiment the number of counts at maximum count line 75 is set at 1000 to assure a statistically valid sampling size. The detector routine 76 is necessary to avoid false reading attributed to noise and like effects. That is, if multi-channel analyzers 73 were turned on and without any gamma rays 13 between detector heads 11, a histogram indicated by dash-line 79 in FIG. 6 would develop. Detector routine 76 prevents noise triggering a spectral energy read-out from any multi-channel analyzer 73. Whether the histogram developed in any multi-channel analyzer 73, is determined valid by detector routine 76 or not, once detector routine 76 senses completion of a channel count, that triggering multi-channel analyzer $73_t$ is reset to zero. The counting routine to develop the histogram for the reset multi-channel starts anew and doesn't affect or impact the counting of any other multi-channel analyzer. The detector routine 76 is an easy approach to build a large data-base which can be accurately sampled to determine that camera 10 is producing signals corresponding to the spectral energy of the gamma radiation being imaged. Once detector routine 76 determines the triggering multi-channel analyzer $73_t$ has sensed a valid event, the count data from the triggering multi-channel analyzer $73_t$ is read out to Compton routine 77 which is perhaps best explained by reference to FIG. 8.

FIG. 8 shows a histogram 71 which would be developed in a triggering multi-channel analyzer $73_t$ if there was not any stray noise influences affecting the energy of gamma rays 13. The histogram 71 would be uniformly centered about its peak energy and have a leading edge portion 71a identical to a trailing edge portion 71b. It has been discovered and verified through observations that the effects of Compton scattering, such as attributed to the patient's fatty tissue, will distort the leading edge of 71a of histogram 71 such as shown by dash line 71d. However, trailing edge portion 71b will not be affected. Thus, when the data from triggering multi-channel analyzer is determined valid, Compton routine 77 determines by sampling one or more leading channels (lower energy than that of triggering channel $74_t$) to determine whether or not Compton scattering has to be accounted for or not in calculate program routine 78. If Compton scattering is significantly present, then calculate routine 78, in accordance with one aspect of the invention, can be employed to analyze histogram 71 from its peak energy only over trailing edge portion 71b which is shown by the shaded area of histogram 71 in FIG. 8. In the preferred embodiment, however, a correction is used.

Calculate routine 78 determines a specific peak energy level for triggering multi-channel analyzer 73t. Those skilled in the art will readily recognize that there are at least a dozen or so techniques which could be used to develop form fitting curves for the histograms developed in multi-channel analyzer 73 and from such curves a peak spectral energy value (as opposed to the range of the channel) can be extrapolated and used to adjust the gain of each triggering PMT 12. All such form fitting techniques are contemplated as falling within the scope of this invention. In the preferred embodiment each channel 74 is assigned a mid-point spectral energy or voltage value and the channels (the triggering channels 74t and the channels on either side $74_{t-1}$ and $74_{t+1}$) are weighted by the number of counts, summed and simply averaged to determine a peak spectral energy. This is in accordance with the general weighting formula:

$$z = \frac{\sum_{i=t-n}^{t+n} E_i \cdot C_i}{\sum_{i=t-n}^{t+n} C_i}$$

where $E_i$=mid point channel energy or voltage value t-n, t+n=channel number from triggering channel $_t$. In the preferred embodiment, $_n$=1 so that the summation is for $74_t$, $74_{t-1}$ and $74_{t+1}$ $C_i$=number of counts for the designated channel If Compton routine 77 determined significant Compton scattering (i.e., recording excessive counts at the channels corresponding to leading edge 71d), then an actual Compton scattering correction is employed. In the preferred embodiment, the "minima" on each side of the peak is determined and a straight line drawn therebetween. The value of the straight line is subtracted from the energy value at each channel location from the spectrum value at that channel location. This is shown approximately in FIG. 8 where line 75a represents a line between the minima on either side of the peak. The spectral energy read at channels $74_{t+1}$ and $74_{t-1}$ are reduced by the energy represented by line 75a at channels $74_{t+1}$ and $74_{t-1}$ and the peak energy of the histogram calculated by the weighted summation discussed above.

The peak energy thus determined in calculate routine 78 is then compared in adjust program 80 to an energy value stored for each PMT 12 (for the specific isotope being imaged stored in a look up table 82 in computer 20) to determine if there is a difference and if the difference exceeds a set amount, then a digital signal is sent to computer 20 for changing the gain voltage set for the triggering PMT 12 in look up table 82.

Those skilled in the art will recognize that the energy of the gamma ray is itself being utilized to determine if each PMT is developing an output or gain which can be directly correlated to the energy of the specific gamma rays being imaged, simultaneously, by camera 10. This means that the system of this invention can be used to initially calibrate camera 10 as well as continually calibrate or adjust for PMT drift during use. For example, and again referring to FIG. 2, a point source from known radiation can be placed between detector heads 11 with collimators 21 removed, or detector heads 11 can be fitted with lead aperture mask 64 for the uniform radiation source as shown and the baseline voltage of power source 26 set as initially explained. Each triggering PMTs multi-channel analyzer 73 will, in turn, produce a spectral energy readout correlated to the energy of the known isotope which is used to adjust the gain from the specific corresponding triggering PMT. More specifically, it is known what the maximum voltage is that can be applied to a specific dynode to produce maximum linear PMT gain. For example, 4.10 volts. When camera 10 is initially calibrated by either a point source or a uniform flood of radiation, computer 20 sends a digital signal to digital to analogue converter 28 which applies this voltage to all PMT's 12. (In the preferred embodiment, an 8 bit signal is used which produces 255 digitized settings incremented over a given voltage range typically 0–5 volts. Thus, one of the 255 signals represents a voltage of 4.10 volts producing optimum PMT gain.) The peak histogram voltage as defined above is compared to the control setting and if the difference exceeds a set range, the look up table value for that specific PMT is changed to reattain 4.10 volt output. (Those skilled in the art will recognize that the histogram voltage does not have to correspond 1 to 1 to the PMT voltage as in the preferred embodiment, but the relationship is linear so that a constant scaling factor is used.) Thus, look up table 82 in computer 20 initially has an 8 bit number corresponding to the optimal, linear gain of each PMT 12 which is constant for each PMT. Any given isotope will then generate a peak histogram voltage which is compared to the set number for each triggering PMT and the difference between the two is used to adjust the set voltage up or down in look up table 82 for that triggering PMT 12. Eventually, a specific look up table 82 is generated for that specific isotope. The next isotope is then placed within camera 10 and a look up table is similarly developed for that isotope, etc. When the camera is imaging, the look up table 82 for that particular isotope is called from memory and the values stored in that table are compared to the peak histogram voltages and the table adjusted accordingly. The same procedure is thus used in either instance. When camera 10 was initially calibrated, the peak histogram voltages were compared to a set PMT voltage in look up table 82 and the table 82 rewritten. When imaging, the peak histogram voltage is compared to the stored voltages generated for look up table 82 during calibration and look up table 82 changed accordingly. Thus, camera 10 is constantly being calibrated during use to maintain its peak PMT gain voltage thus obviating any need to recalibrate camera 10.

Since the multi-channel analyzers automatically reset when an event is detected, the effect of adjusting any one PMT's gain on the gain of other PMTs 12 is eventually compensated. That is, the hunting or the iteration process is automatic and, as noted, it typically takes about 10 to 15 minutes to initially calibrate camera 10 for any specific isotope. Once each PMTs gain values have been set and stored in look up tables 82 in computer 20, the invention uses adjust program 80 in digital signal processor 50 to compare the spectral energy of any trigger multi-channel analyzer 73 with the values stored in look up table 82 within computer 20 and if there is a deviation beyond a set limit, look up table 82 is changed and the gain of the corresponding triggering PMT 12 is changed by computer 20 transmitting its signal to a digital to analogue converter 28 to gain control circuit 32 as previously described.

Figure 9:
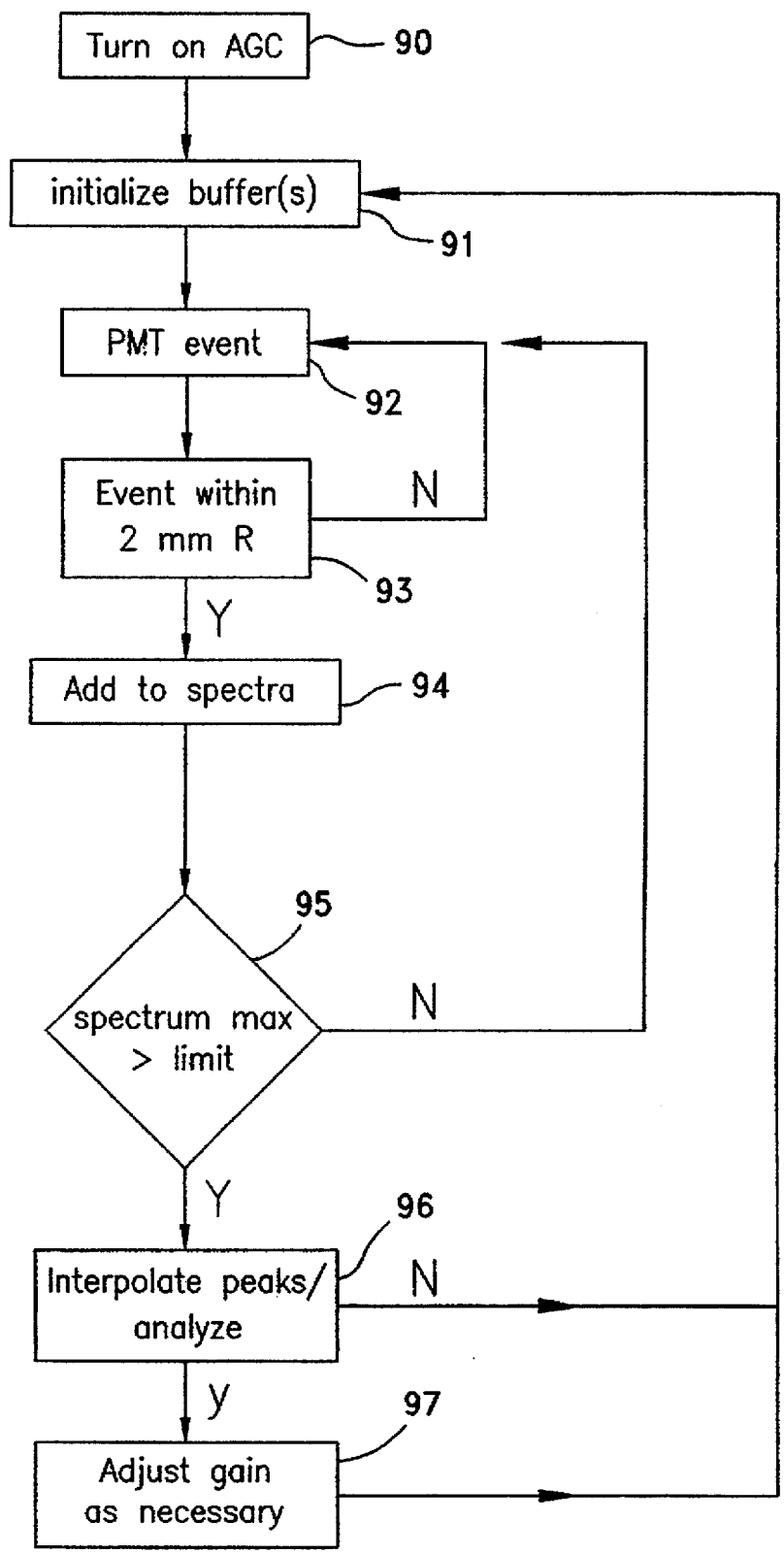
FIG. 9 is a flow chart showing the automatic calibration process of the invention; and, FIGS. 10 and 11 are partial gamma camera schematics showing the invention used in other conventional gamma cameras.

Referring now to FIG. 9, there is shown the flow chart of the invention. The automatic gain control feature is turned on at block 90. Multi-channel analyzers 73 are initialized and set to zero at block 91. Detection of a PMT event occurs within event detection circuit 35 and is processed through weighting table 52 which establishes a scintillation event shown at block 92. The scintillation event is next checked to determine if it is within a 2 mm radius of a triggering PMT center through center routine 72 as shown by block 93. If it is, the event is added to the triggering PMT's multi-channel analyzer 73 in block 94. Each multi-channel analyzer 73 is continuously monitored by detector program 76 to determine if the maximum number of counts has occurred for any given channel as shown in block 95. When detector program 76 senses a channel has reached its maximum number, detector program 76 further determines if the histogram 71 is valid or not. If invalid, the triggering multi-channel analyzer 73, is reset to zero. If valid, Compton program 77 and calculate program 78 determine the peak spectral energy of histogram 71. Peak spectral energy is then read out at block 96 to calculate program 80 which adjusts the gain of the triggering PMT if necessary at block 97.

Figure 10:
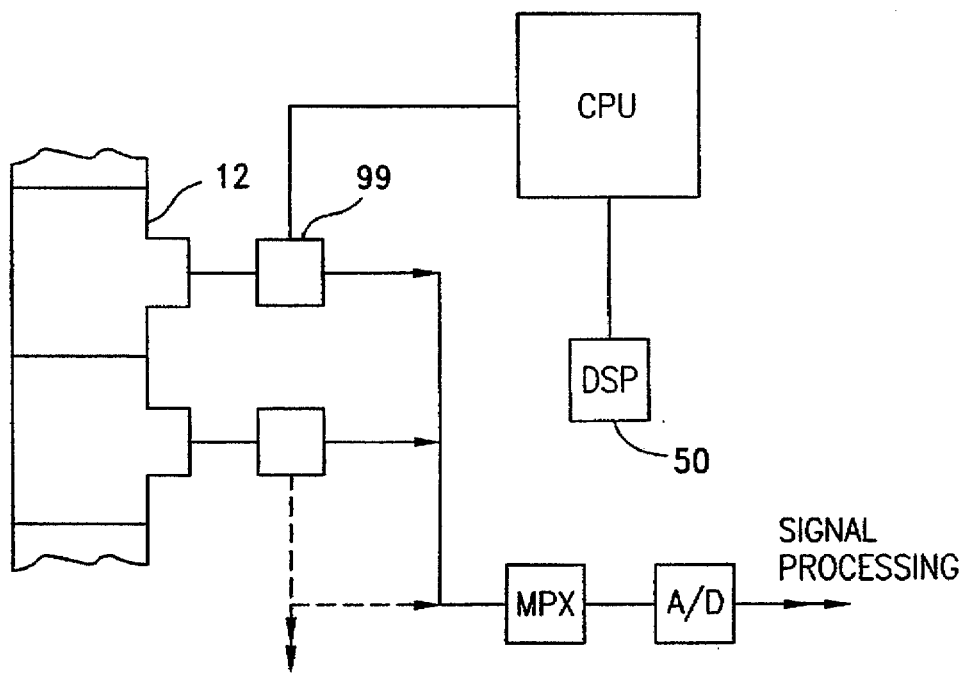
Figure 11:
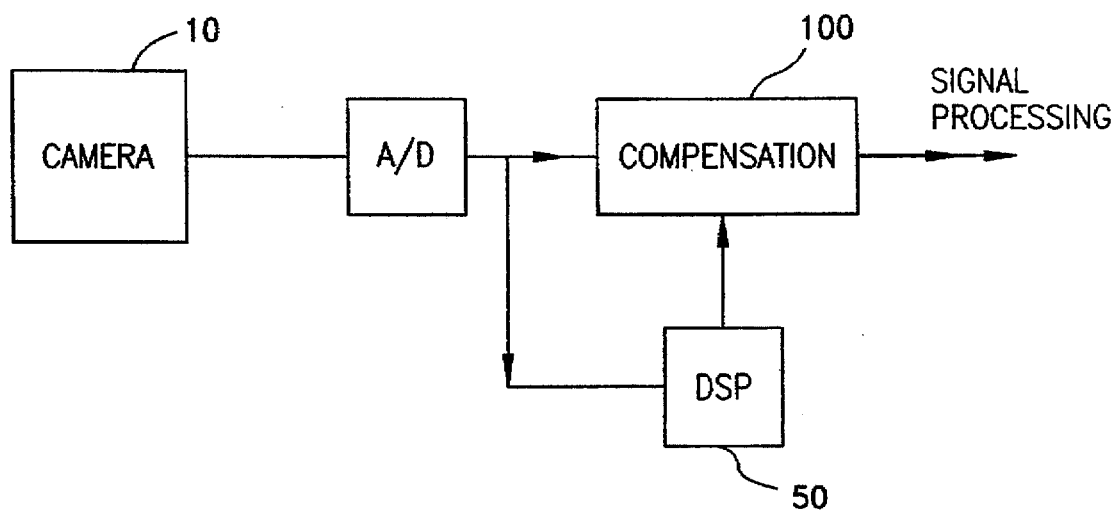

FIGS. 10 and 11 illustrate general schematics of alternative embodiments of the invention. In conventional cameras, an amplifier 99 as shown in FIG. 10 is provided to amplify the analogue signal produced by each PMT 12. The gain of PMT 12 can be controlled by simply adjusting amplifier 99. For example, in the preferred embodiment the adjustment would be made at gain control circuit 32. In other conventional cameras 10, no adjustment whatsoever is made at PMTs 12 but whatever PMT signals are developed, the signals are modified in a compensation circuit 100 shown for conventional gamma camera signal processing scheme illustrated in FIG. 11. Compensation circuit 100, in turn, contains look up tables corresponding to each radioactive isotope for adjusting the PMT signals. Accordingly, the digital signal processor 50 would adjust the look up tables in compensation circuit 100 on a PMT by PMT basis and compensation circuit 100 would adjust the signals for an appropriate gain. As discussed previously, while the invention can be utilized in the alternative embodiments and a significant improvement in the nuclear camera art will result therefrom, the preferred embodiment adjusts the gain of each PMT so that the PMT can not drift to the point where the camera has to be recalibrated. In the alternative embodiments the PMTs can drift to a non-linear output response requiring recalibration. In the preferred embodiment, the dynode of each PMT is constantly checked and adjusted during camera operation to keep each PMT output linear. While the concept of electronically adjusting the dynode automatically during calibration was patented in my prior invention, this invention discloses a system for automatically collecting data which instructs the system of my prior invention to make the correction on the fly. While this invention can be used with conventional systems as shown in the alternative embodiments, the use of this invention to calibrate individual PMTs on the fly as disclosed in the preferred embodiment is a separately patentable aspect of the invention.

As thus described, the invention is self-correcting and automatically and continuously calibrates camera 10 during imaging. Further, tests have shown that the camera is calibrated and recalibrated for all PMTs in the PMT matrix in time spans of about 10 to 15 minutes. Thus, the end user does not have to periodically recalibrate the camera or pay service fees to have a field technician periodically recalibrate the camera, nor does the camera have to suffer any down time for calibration.

Figure 7:
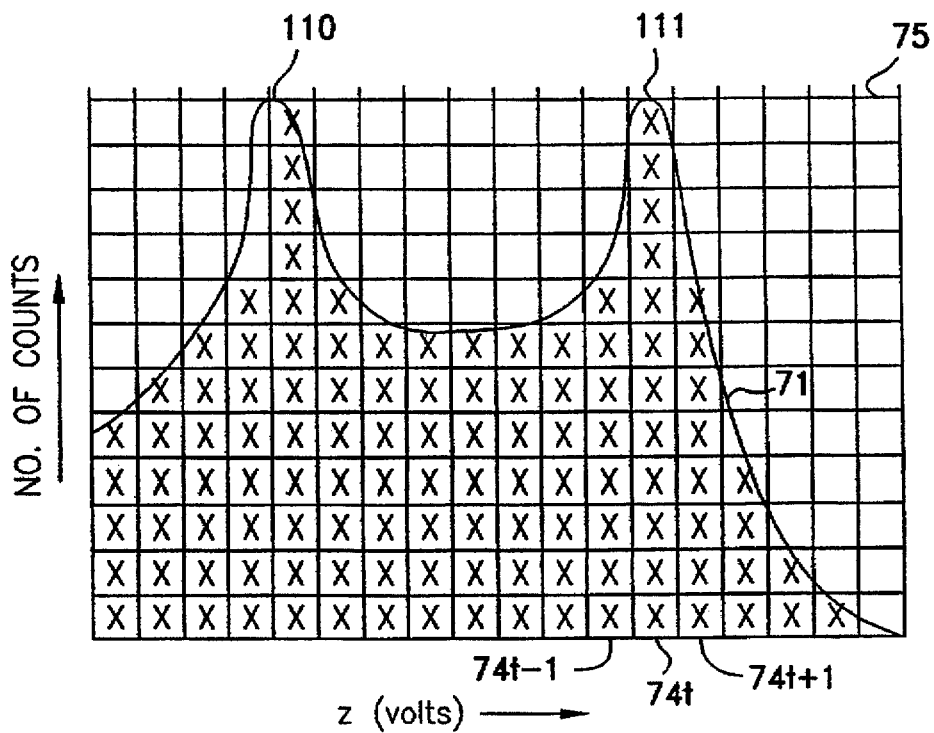
FIG. 7 is a multi-channel analyzer histogram developed during dual isotope imaging.

The invention has been described with reference to a preferred embodiment. Obviously, alterations and modifications will become apparent to those skilled in the art upon reading and understanding the Detailed Description above. It is possible to calibrate camera 10 during dual isotope imaging such as with technetium and thallium isotopes. Histograms such as shown in FIG. 7 are produced and peak channels such as those occurring at positions 110 and 111 are produced to determine that spectral energies of the thallium and technetium rays, respectively. Standard practice is to adjust the PMT on the basis of the highest peak energy, i.e., the technetium ray. However, it is conceivable that other schemes can be used and, if so, this invention lends itself to such techniques because it discriminates or identifies the energies of both rays. It is intended to include all such modification and alterations insofar as they come within the scope of the present invention.

Having thus defined the invention, it is claimed:

1. A method for individually adjusting gain signals of the PMTs in a gamma camera on the fly in which any given PMT, a triggering PMT, upon detecting a scintillation event producing a signal above a set limit triggers a grouping of a selected plurality of PMTs associated with said triggering PMT and said triggering PMT's signal along with the grouped PMTs' signals are individually digitized into a set of grouped signals, each having an x,y position component and a z spectral energy component which are weighted to produce a single digitized scintillation event signal corresponding to a pixel of a scintillation image, said method comprising the steps of:

a) providing a multi-channel analyzer for each PMT with each channel of each analyzer assigned a range of spectral energies;

b) counting the z component of the scintillation event signal into the channel of the triggering PMT's analyzer whose range encompasses the z component if the x,y position of said scintillation event signal is within a set distance from the center of the face of said triggering PMT;

c) calculating and reading out the peak z energy recorded in said triggering PMT's analyzer when the number of scintillation event signals stored therein reaches a set number; and, d) using said peak z energy to adjust said camera's signals attributed to said triggering PMT which produce said scintillation image.

2. The method of claim 1 wherein said peak z energy is used to set the gain of said triggering PMT whereby said camera's signals which produce said scintillation image are adjusted.

3. The method of claim 2 further including within step (d) the additional step of:

comparing the read out z energy in step (c) with a z energy previously stored for said triggering PMT to set, when a difference beyond a set amount is detected, the gain of said triggering PMT while said camera is simultaneously imaging the radiation.

4. The method of claim 1 further including the additional step (e) of resetting any given multi-channel analyzer to zero after completing step (c) for said given multi-channel analyzer while continuing step (b) for any multi-channel analyzer which has not accumulated sufficient counts to progress to step (c).

5. The method of claim 4 wherein step (c) includes the steps of i) determining if any channel, a triggering channel, in said multi-channel analyzer reaches a set number of counts and ii) determining if either one of the two channels adjacent said triggering channel have stored therein a number of counts which is at least less than eighty per cent (80%) before calculating and reading out said peak z energy.

6. The method of claim 5 further including the step of resetting said multi-channel analyzer to zero if, in step (c), the number of counts in both of the channels adjacent to said triggering channel is greater than 80% of the counts recorded in said triggering channel, whereupon step (b) is continuously performed on the reset multi-channel analyzer until step (c) is reached.

7. The method of claim 5 wherein said peak z energy is determined in step c in accordance with the formula:

$$z = \frac{\sum_{t-n}^{t+n} E_i \cdot C_i}{\sum_{t-n}^{t+n} C_i}$$

where $E_i$=mid point channel energy, t−n,t+n=channel number from triggering channel, $C_i$=number of counts for the designated channel.

8. The method of claim 7 further including calculating said peak energy in step (c) by adjusting the number of counts recorded in channels t+n and t−n to a lesser number to account for noise distortions attributed to Compton scattering effects.

9. The method of claim 2 wherein said camera is initially calibrated by i) removing the collimators from the camera's detector head and ii) placing a point source of known radiation between said heads whereupon step (c) will set the gain of any given triggering PMT and storing the value of said gain for any given triggering PMT in a look up table until all PMTs have been triggered.

10. The method of claim 2 wherein said camera is initially calibrated by i) fitting a lead aperture mask about the cameras and ii) placing a known source of gamma radiation if a specific size and shape between the camera's detector heads to produce a flood of gamma rays uniformly impinging each PMT whereupon step (c) will set the gain of any given triggering PMT and storing the value of said gain for any given triggering PMT in a look up table until all PMTs have been triggered.

11. The method of claim 3 wherein the voltage potential of a specific dynode in a triggering PMT is set at a potential correlated to said peak z energy read out of said triggering PMT's multi-channel analyzer in step (c).

12. The method of claim 2 wherein the voltage potential of a specific dynode in a triggering PMT is set at a potential correlated to said peak z energy read out of said triggering PMT's multi-channel analyzer in step (c).

13. The method of claim 1 wherein said camera has a compensation circuit including spectral energy look up tables downstream of said PMTs for adjusting the z component signal of each PMT and changing said look up table for any triggering PMT whose multi-channel analyzer has a z component different by a set amount from the spectral energy stored in said spectral energy look up table for said triggering PMT.

14. The method of claim 1 wherein said camera has a gain amplification circuit for increasing the intensity of said z component of any given PMT by a value stored in a table corresponding to the gain of any given PMT and changing said look up table for any triggering PMT whose multi-channel analyzer has a z component different by a set amount from that stored in said look up table for said triggering PMT.

15. The method of claim 1 wherein said set distance is about four mm and said set number of scintillation event signals is about 1,000 in number whereby a statistically valid sample is obtained.

16. The method of claim 15 wherein said selected plurality equals 19 in number.

17. In a gamma camera including a first plurality of PMTs, each generating analogue signals in response to scintillations produced by gamma rays; detection means triggered when any given PMT, a triggering PMT, generates an analogue signal above a set limit indicative of a scintillation event; clustering means for grouping analogue signals from a smaller second plurality of PMTs within said first plurality and generally adjacent said triggering PMT to define along with said triggering PMT's analogue signal a clustered group of PMT analogue signals; digitizing means for converting each PMT analogue signal in said clustered group into a digital signal having an x,y position component and a spectral energy z component; weighting means for factoring said clustered group of digital signals to produce a single, digital scintillation event signal and imaging means for producing a scintillation image from a plurality of said scintillation event signals, comprising:

a) each PMT having a corresponding multi-channel analyzer, each analyzer having a plurality of channels with each channel divided into set ranges of spectral energies;

b) accessing means for counting said z component of said scintillation event signal into the channel corresponding to the intensity thereof for said triggering PMT's multi-channel analyzer when the x,y position component of said scintillation event signal is within a set distance from the center of said triggering PMT;

c) read out means for recording the peak spectral energy within said triggering PMT's multi-channel analyzer when the number of events stored therein have reached a set number; and, d) comparing means for comparing the z component of the read out multi-channel analyzer with a previously stored z component associated with said triggering PMT whereby the difference signal, if any, is used to adjust the gain of said triggering PMT on the fly if the difference between said z components exceeds a set value.

18. The improvement of claim 17 wherein said read out means further includes triggering means to determine when any given channel, a triggering channel, in said triggering PMT's multi-channel analyzer reaches a set number and verifying means to determine if either channel adjacent said triggering channel has a count number no greater than 80% of the counts recorded in said triggering channel.

19. The improvement of claim 18 wherein said either channel has a count number no greater than 70% of the counts recorded in said triggering channel.

20. The improvement of claim 18 further including reset means for resetting any given triggering PMT multi-channel analyzer to zero after said read out means have read out the counts in said given triggering PMT multi-channel analyzer.

21. The improvement of claim 17 further including means to set the voltage potential of a specific dynode in accordance with a signal generated from a spectral energy look up table under computer control and said comparing means effective to rewrite said look up table for any given triggering PMT whose peak spectral energy determined by said triggering channel's multi-channel analyzer differs by a set amount from that stored in said look up table for said given triggering PMT.

22. A gamma camera comprising:
a) scintillation means receiving radiation and transmitting light in response thereto:
b) a first plurality of PMTs adjacent said scintillation means and generating analogue signals indicative of the z energy of the light emanating from said scintillation means;
c) detecting means to detect when any given one PMT of said first PMT plurality has triggered a z signal in excess of a set energy, said given PMT being a triggering PMT;
d) means for grouping a smaller, second plurality of PMTs generally adjacent said triggering PMT and simultaneously detecting the z signals of each PMT in said second plurality;
e) an analogue to digital converter for generating from said analogue signals a digitized x,y position signal and z intensity signal for said triggering PMT and for each PMT in said second plurality;
f) means to weight said digitized signals from said triggering PMT and each second plurality PMT to determine a scintillation event x,y position and z intensity signal;
g) imaging means to convert said scintillation event signal to a pixel for CRT display;
h) a multi-channel analyzer for each PMT in said first plurality, each multi-channel analyzer having a plurality of z energy channels, each channel set at a discrete energy range;
i) discriminating means for simultaneously counting the z energy of a scintillation signal at a channel within the range of said scintillation z signal for the triggering PMT multi-channel analyzer if the x,y position signal of said scintillation event is within a set distance from the center of said triggering PMT;
j) read out means for determining the peak spectral energy from said triggering PMT multi-channel analyzer when the total number of counts in said triggering PMT multi-channel analyzer reaches a set limit; and,
k) means to compare the peak spectral energy for a triggering PMT determined by its multi-channel analyzer with a prior signal for said triggering PMT whereby said camera's gain for said triggering PMT is adjusted on the fly.

23. The gamma camera of claim 22 wherein said read out means further including triggering means to determine when any given channel, a triggering channel, in said triggering PMT's multi-channel analyzer reaches a set number and verifying means to determine if either channel adjacent said triggering channel has a count number not greater than 70% of the counts recorded in said triggering channel.

24. The gamma camera of claim 23 further including reset means for resetting any given triggering PMT multi-channel analyzer to zero after said read out means have read out the counts in said given triggering PMT multi-channel analyzer.

25. The gamma camera of claim 22 further including means to set the voltage potential of a specific dynode in accordance with a signal generated from a spectral energy look up table under computer control and said comparing means effective to rewrite said look up table for any given triggering PMT whose maximum spectral energy determined by said triggering channel's multi-channel analyzer differs by a set amount from that stored in said look up table for said given triggering PMT.

26. The gamma camera of claim 23 wherein said read out means determines said peak energy in accordance with the formula:

$$z = \frac{\sum_{t-n}^{t+n} E_i \cdot C_i}{\sum_{t-n}^{t+n} C_i}$$

where
$E_i$=mid point channel energy,
$t-n, t+n$=channel number from triggering channel,
$C_i$=number of counts for the designated channel.

27. The gamma camera of claim 26 wherein said read out means adjusts the counts of each of the adjacent channels $t_{n+1}$ and $t_{n-1}$ to a lesser number to account for effects attributed to Compton scattering.

* * * * *